(12) United States Patent
Francois

(10) Patent No.: US 8,723,148 B2
(45) Date of Patent: May 13, 2014

(54) SAFETY NET SYSTEM

(76) Inventor: Norma Francois, Brooklyn, NY (US)

( * ) Notice: Subject to any disclaimer, the term of this patent is extended or adjusted under 35 U.S.C. 154(b) by 0 days.

(21) Appl. No.: 13/585,883

(22) Filed: Aug. 15, 2012

(65) Prior Publication Data

US 2013/0098672 A1    Apr. 25, 2013

Related U.S. Application Data

(60) Provisional application No. 61/627,842, filed on Oct. 19, 2011.

(51) Int. Cl.
*G21F 1/00*    (2006.01)

(52) U.S. Cl.
USPC .................. 250/516.1; 250/519.1; 250/505.1

(58) Field of Classification Search
USPC ..................... 250/505.1, 515.1, 516.1, 519.1
See application file for complete search history.

(56) References Cited

U.S. PATENT DOCUMENTS

| | | | |
|---|---|---|---|
| 5,073,984 A | 12/1991 | Tone et al. | |
| 5,419,342 A * | 5/1995 | Scott | 128/846 |
| 5,570,476 A | 11/1996 | Olive | |
| 5,621,188 A | 4/1997 | Lee et al. | |
| 5,882,242 A * | 3/1999 | Hardy | 450/93 |
| 7,276,716 B1 * | 10/2007 | Munro, III | 250/515.1 |
| 8,354,658 B1 * | 1/2013 | Smith et al. | 250/516.1 |
| 2002/0148980 A1 * | 10/2002 | Cadwalader et al. | 250/515.1 |
| 2010/0060431 A1 * | 3/2010 | Stevenson et al. | 340/10.1 |
| 2010/0308238 A1 * | 12/2010 | Bustamante et al. | 250/515.1 |
| 2011/0095209 A1 * | 4/2011 | Cadwalader et al. | 250/519.1 |

* cited by examiner

*Primary Examiner* — Nicole Ippolito
(74) *Attorney, Agent, or Firm* — Emery L. Tracy; Ruth Eure

(57) ABSTRACT

A safety net system for blocking electromagnetic field (EMF) exposure from electronic devices is provided. The safety net system comprises a hair net for covering at least a portion of a head and a body net having a back portion for covering an upper back and shoulders, a first front portion for covering a right breast, and a second front portion covering a left breast. A first anti-EMF chip is mounted to the hair net, a second anti-EMF chip is mounted to the back portion, a third anti-EMF chip is mounted to the first front portion, and a fourth anti-EMF chip mounted to the second front portion. Upon positioning the hair net over the at least a portion of the head and upon draping the body net over the shoulders thereby covering the upper back and breasts, the anti-EMF chips block and shield EMF radiation from reaching the body part.

20 Claims, 1 Drawing Sheet

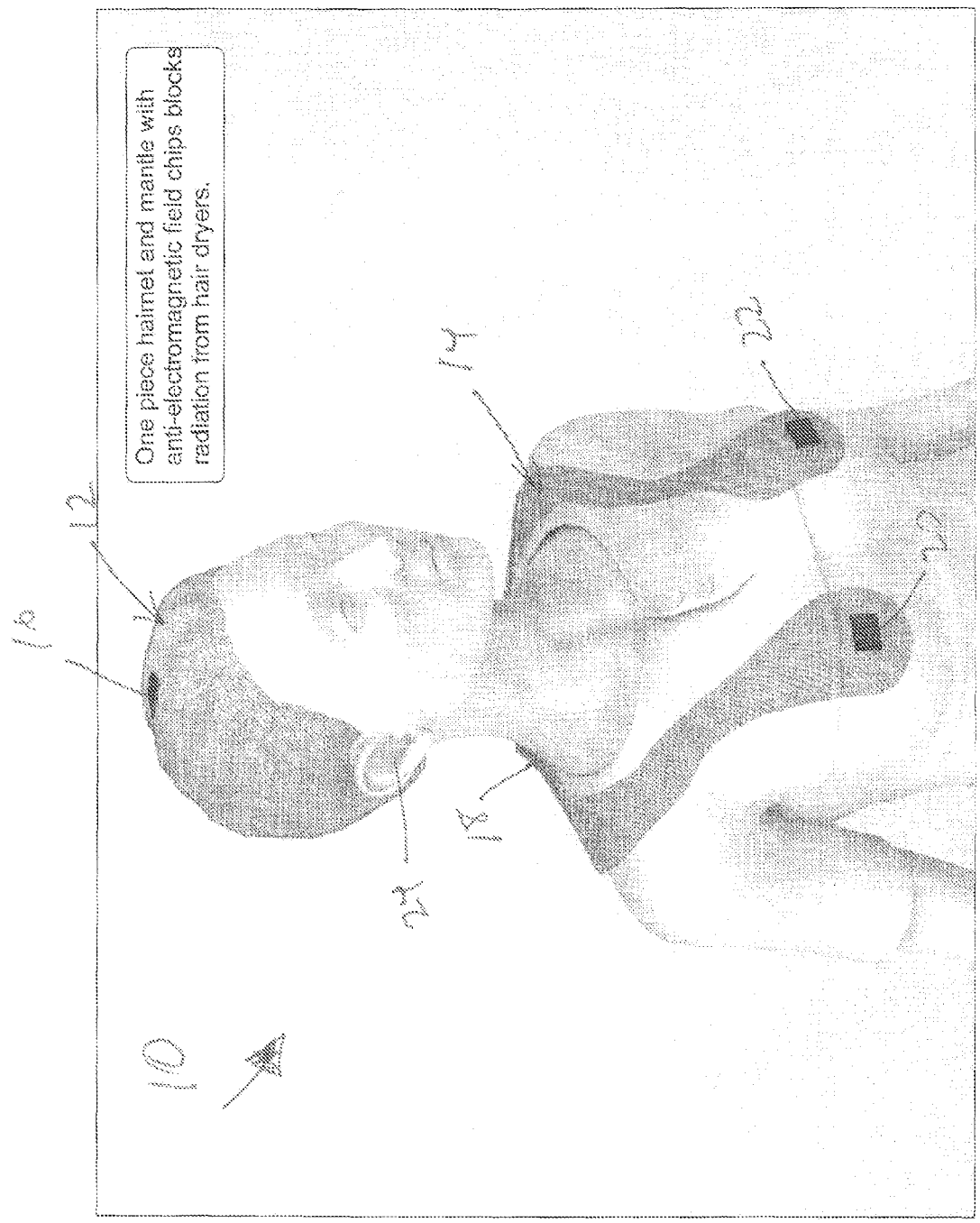

SAFETY NET SYSTEM

The present application claims the benefit of priority of pending provisional patent application Ser. No. 61/627,842, filed on Oct. 19, 2011, entitled "Safety Net".

BACKGROUND OF THE INVENTION

1. Field of the Invention

This invention relates generally to a safety net system and, more particularly, the invention relates to a safety net system for blocking possible EMF exposure from home and salon hair dryers and handheld blow dryers.

2. Description of the Prior Art

Since EMFs contain radiation, much effort is currently being directed towards the study of electromagnetic fields in relation to cancer, along with other maladies such as Alzheimer's disease, chronic fatigue syndrome, headaches, and high blood pressure, just to name a few examples. While no obvious adverse effect of exposure to low level radiofrequency fields has been discovered to date, studies in search for possible carcinogenic (cancer-producing) effects of power frequency fields are continuing, given public concerns primarily regarding the safety of cellular telephones, as well as other small appliances used by the populace on a regular basis. In the meantime, people want to err on the side of caution, and seek ways of preventing EMF exposure when it is not practical for them to completely avoid using devices and appliances that emit these fields.

SUMMARY

The present invention is a safety net system for blocking electromagnetic field (EMF) exposure from electronic devices. The safety net system comprises a hair net for covering at least a portion of a head and a body net having a back portion for covering an upper back and shoulders, a first front portion for covering a right breast, and a second front portion covering a left breast. A first anti-EMF chip is mounted to the hair net, a second anti-EMF chip is mounted to the back portion of the body net, a third anti-EMF chip mounted to the first front portion of the body net, and a fourth anti-EMF chip mounted to the second front portion of the body net. Upon positioning the hair net over the at least a portion of the head and upon draping the body net over the shoulders thereby covering the upper back and breasts, the anti-EMF (electromagnetic field) chips block and shield electromagnetic field radiation from reaching the body part below the hair net and the body net.

BRIEF DESCRIPTION OF THE DRAWINGS

FIG. 1 is a perspective view illustrating a safety net system, constructed in accordance with the present invention.

DETAILED DESCRIPTION OF THE PREFERRED EMBODIMENTS

As illustrated in FIG. 1, the present invention is a safety net system, indicated generally at 10, for blocking possible EMF exposure from home and salon hair dryers and handheld blow dryers. The safety net system 10 of the present invention is a specially designed upper body covering outfitted with a series of anti-EMF (electromagnetic field) chips, placed in strategic areas to protect the head, neck, and the chest.

The safety net system 10 of the present invention is a one-piece, cotton mesh hair net 12 that shields the head and a one-piece, cotton mesh body net 14 that shields the neck and sensitive areas of the chest, such as the breasts. The safety net system 10 features a total of four (4) anti-EMF chip devices: chip 1 16 is positioned in the middle of the hair net where it covers the crown of the head; chip 2 18 is located at the center of the portion of the body net covering the back of the neck to block exposure to the neck and spine; and chips 3 20 and 4 22 would be placed at the body net's bottom where the body net 14 shields each breast from possible exposure. The anti-EMF chips are designed to act as a blocking shield between magnetic field radiation source and the part of the body below the shield. Generally speaking, a layer of high-tech radiation shielding material incorporated into the chip contains the field and reduces heat by increasing dissipation to the environment and away from the body. In addition to the primary purpose, a pair of oval shaped, cotton pads 24 can be provided to cover the ears while worn so that possible irritation to the ears caused by the heat of hair dryers can be avoided.

The safety net system 10 of the present invention allows a user to don the hair set 12 and body net 14 to protect susceptible areas of the body in a matter of seconds. As a result, men and women who are concerned with the appearance of the hair, not to mention their health, are able to utilize both stationary and handheld hair dryers with confidence. While the safety net system 10 is perfect for home use, salons that offer the net to their patrons are sure to be appreciated by their clientele.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein may be suitably practiced in the absence of the specific elements which are disclosed herein.

What is claimed is:

1. A safety net system for blocking electromagnetic field (EMF) exposure from electronic devices, the safety net system comprising:
   a hair net for covering at least a portion of a head, the hair net having an outer hair net perimeter;
   a body net having a back portion for covering an upper back and shoulders, a first front portion for covering a right breast, and a second front portion covering a left breast, the body net having an outer body net perimeter;
   a first anti-EMF chip mounted completely within the outer hair net perimeter of the hair net;
   a second anti-EMF chip mounted to the back portion completely within the outer body net perimeter of the body net;
   a third anti-EMF chip mounted to the first front portion completely within the outer body net perimeter of the body net; and
   a fourth anti-EMF chip mounted to the second front portion completely within the outer body net perimeter of the body net;
   wherein upon positioning the hair net over the at least a portion of the head and upon draping the body net over the shoulders thereby covering the upper back and breasts, the anti-EMF (electromagnetic field) chips block and shield electromagnetic field radiation from reaching the body part below the hair net and the body net.

2. The safety net system of claim 1 wherein the hair net covers an upper head, the first anti-EMF chip mounted at a crown of the upper head.

3. The safety net system of claim 1 wherein the second anti-EMF chip is positioned in a center of the back portion of the body net.

4. The safety net system of claim 1 wherein the third anti-EMF chip is positioned over the right breast.

5. The safety net system of claim 1 wherein the fourth anti-EMF chip is positioned over the left breast.

6. The safety net system of claim 1 wherein the hair net and the body net is constructed of a cotton mesh material.

7. The safety net system of claim 1 and further comprising:
a layer of radiation shielding material incorporated into each of the anti EMF chips that contain the electromagnetic field and reduces heat by increasing dissipation to the environment and away from the body.

8. The safety net system of claim 1 and further comprising:
a pair of oval shaped, cotton pads positionable over the ears.

9. A safety net system for blocking electromagnetic field (EMF) exposure from electronic devices, the safety net system comprising:
a hair net for covering at least a portion of a head;
a body net having a back portion for covering an upper back and shoulders, a first front portion for covering a right breast, and a second front portion covering a left breast;
a separate and distinct first anti-EMF chip mounted to the hair net and positionable at a crown of the upper head;
a separate and distinct second anti-EMF chip mounted to the back portion of the body net and positionable in a center of the back portion of the body net;
a separate and distinct third anti-EMF chip mounted to the first front portion of the body net and positionable over the right breast; and
a separate and distinct fourth anti-EMF chip mounted to the second front portion of the body net and positionable over the left breast;
wherein upon positioning the hair net over the at least a portion of the head and upon draping the body net over the shoulders thereby covering the upper back and breasts, the anti-EMF (electromagnetic field) chips block and shield electromagnetic field radiation from reaching the body part below the hair net and the body net.

10. The safety net system of claim 9 wherein the hair net and the body net is constructed of a cotton mesh material.

11. The safety net system of claim 9 and further comprising:
a layer of radiation shielding material incorporated into each of the anti EMF chips that contain the electromagnetic field and reduces heat by increasing dissipation to the environment and away from the body.

12. The safety net system of claim 9 and further comprising:
a pair of oval shaped, cotton pads positionable over the ears.

13. A method for blocking electromagnetic field (EMF) exposure from electronic devices, the method comprising:
providing a hairnet;
covering at least a portion of a head with the hair net;
providing a body net having a back portion for covering an upper back and shoulders, a first front portion for covering a right breast, and a second front portion covering a left breast;
covering an upper back with the back portion;
covering a right breast with the first front portion;
covering a left breast with the second front portion;
mounting a first anti-EMF chip to the hair net;
mounting a second anti-EMF chip to the back portion of the body net;
mounting a third anti-EMF chip to the first front portion of the body net;
mounting a fourth anti-EMF chip to the second front portion of the body net;
positioning the hair net over the at least a portion of the head;
draping the body net over the shoulders and covering the upper back and breasts; and
blocking and shielding electromagnetic field radiation from reaching the body part below the hair net and the body net.

14. The method of claim 13 and further comprising:
covering the upper head with the hair net; and
mounting the first anti-EMF chip at a crown of the upper head.

15. The method of claim 13 and further comprising:
positioning the second anti-EMF chip in a center of the back portion of the body net.

16. The method of claim 13 and further comprising:
positioning the third anti-EMF chip over the right breast.

17. The method of claim 13 and further comprising:
positioning the fourth anti-EMF chip over the left breast.

18. The method of claim 13 and further comprising:
constructing the hair net and the body net of a cotton mesh material.

19. The method of claim 13 and further comprising:
providing a layer of radiation shielding material incorporated into each of the anti EMF chips that contain the electromagnetic field and reduces heat by increasing dissipation to the environment and away from the body.

20. The method of claim 13 and further comprising:
positioning a pair of oval shaped, cotton pads over the ears.

* * * * *